(12) United States Patent
Thalacker et al.

(10) Patent No.: US 11,160,733 B2
(45) Date of Patent: Nov. 2, 2021

(54) DENTAL ADHESIVE COMPOSITION, PREPARATION AND USE THEREOF

(71) Applicant: 3M INNOVATIVE PROPERTIES COMPANY, St. Paul, MN (US)

(72) Inventors: Christoph Thalacker, Weilheim (DE); Henry Loll, Gilching (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 16/613,384

(22) PCT Filed: May 8, 2018

(86) PCT No.: PCT/US2018/031548
§ 371 (c)(1),
(2) Date: Nov. 13, 2019

(87) PCT Pub. No.: WO2018/213060
PCT Pub. Date: Nov. 22, 2018

(65) Prior Publication Data
US 2020/0069532 A1 Mar. 5, 2020

(30) Foreign Application Priority Data
May 15, 2017 (EP) .................................. 17170973

(51) Int. Cl.
*A61K 6/30* (2020.01)
*C07F 7/08* (2006.01)
*C08F 20/06* (2006.01)
*C08F 30/02* (2006.01)
*C08F 130/02* (2006.01)
*C08K 3/34* (2006.01)
*A61K 6/887* (2020.01)

(52) U.S. Cl.
CPC .............. *A61K 6/30* (2020.01); *C07F 7/081* (2013.01); *C08F 20/06* (2013.01); *C08F 30/02* (2013.01); *C08F 130/02* (2013.01); *A61K 6/887* (2020.01); *C08K 3/34* (2013.01)

(58) Field of Classification Search
CPC ...................................................... A61K 6/887
See application file for complete search history.

(56) References Cited

U.S. PATENT DOCUMENTS

| 4,256,623 | A | 3/1981 | Junger |
|---|---|---|---|
| 4,259,075 | A | 3/1981 | Yamauchi |
| 4,499,251 | A | 2/1985 | Omura |
| 4,503,169 | A | 3/1985 | Randklev |
| 4,537,940 | A | 8/1985 | Omura |
| 4,539,382 | A | 9/1985 | Omura |
| 4,642,126 | A | 2/1987 | Zador |
| 4,652,274 | A | 3/1987 | Boettcher |
| 4,673,354 | A | 6/1987 | Culler |
| 4,695,251 | A | 9/1987 | Randklev |
| 4,795,823 | A | 1/1989 | Schmitt |
| 4,798,536 | A | 1/1989 | Katz |
| 4,872,936 | A | 10/1989 | Engelbrecht |
| 5,130,347 | A | 7/1992 | Mitra |
| 5,530,038 | A | 6/1996 | Yamamoto |
| 5,996,796 | A | 12/1999 | Kvitrud |
| 5,998,495 | A | 12/1999 | Oxman |
| 6,025,406 | A | 2/2000 | Oxman |
| 6,043,295 | A | 3/2000 | Oxman |
| 6,084,004 | A | 7/2000 | Weinmann |
| 6,105,761 | A | 8/2000 | Peuker |
| 6,187,833 | B1 | 2/2001 | Oxman |
| 6,387,981 | B1 | 5/2002 | Zhang |
| 6,444,725 | B1 | 9/2002 | Trom |
| 6,458,868 | B1 | 10/2002 | Okada |
| 6,572,693 | B1 | 6/2003 | Wu |
| 6,730,156 | B1 | 5/2004 | Windisch |
| 6,899,948 | B2 | 5/2005 | Zhang |
| 7,776,936 | B2 | 8/2010 | Tanaka |
| 7,968,617 | B2 * | 6/2011 | Thalacker ................ A61K 6/30 523/118 |
| 8,029,613 | B2 | 10/2011 | Tanaka |
| 8,211,956 | B2 | 7/2012 | Bock |
| 8,710,115 | B2 | 4/2014 | Thalacker |
| 2003/0166737 | A1 | 9/2003 | Dede |
| 2004/0206932 | A1 | 10/2004 | Abuelyaman |

(Continued)

FOREIGN PATENT DOCUMENTS

| EP | 0712622 | 5/1996 |
|---|---|---|
| EP | 1051961 | 11/2000 |

(Continued)

OTHER PUBLICATIONS

Faulkner, "Silane Coupling Agents in Stainless Steel and Polymethyl Methacrylate Systems", Australian Dental Journal, 1975, pp. 86-88, XP055419848.

(Continued)

*Primary Examiner* — Michael F Pepitone
(74) *Attorney, Agent, or Firm* — Ashley M. Dreis

(57) ABSTRACT

The invention relates to a dental adhesive composition comprising ethylenically unsaturated component(s) with acidic moiety, ethylenically unsaturated component(s) without acidic moiety, water, sensitizing agent(s), reducing agent(s), a silane composition comprising (meth)acrylate functional silane(s) and amino functional silane(s). This composition is in particular useful for adhesively fixing dental restorations based on lithium disilicate and other glass ceramic materials to dental surfaces.

14 Claims, No Drawings

(56) References Cited

U.S. PATENT DOCUMENTS

| | | | |
|---|---|---|---|
| 2005/0165129 A1* | 7/2005 | Moszner | A61K 6/20 523/115 |
| 2005/0252413 A1 | 11/2005 | Kangas | |
| 2005/0252414 A1 | 11/2005 | Craig | |
| 2005/0256223 A1 | 11/2005 | Kolb | |
| 2015/0374465 A1 | 12/2015 | Burke | |
| 2016/0022549 A1 | 1/2016 | Catel | |
| 2016/0250107 A1 | 9/2016 | Kita | |

FOREIGN PATENT DOCUMENTS

| | | |
|---|---|---|
| EP | 2628476 | 8/2013 |
| JP | 2008001624 | 1/2008 |
| JP | 4948915 | 3/2012 |
| WO | WO 2003-063804 | 8/2003 |
| WO | WO 2005-018581 | 3/2005 |
| WO | WO 2011-056814 | 5/2011 |
| WO | WO 2012-125885 | 9/2012 |

OTHER PUBLICATIONS

Lung, "Aspects of Silane Coupling Agents and Surface Conditioning in Dentistry: An Overview", Dental Materials, 2012, vol. 28, pp. 467-477.

Matinlinna, "An Introduction to Silanes and Their Clinical Applications in Dentistry", The International Journal of Prosthodontics, 2004, vol. 17, No. 02, pp. 155-164.

International Search Report for PCT International Application No. PCT/US2018/031548, dated Sep. 13, 2018, 5 pages.

Ishida et al., "The Structure of an Aminosilane Coupling Agent in Aqueous Solutions and Partially Cured Solids," 1982, *Journal of Polymer Science: Polymer Physics Edition*, 20:701-18.

\* cited by examiner

DENTAL ADHESIVE COMPOSITION, PREPARATION AND USE THEREOF

CROSS REFERENCE TO RELATED APPLICATIONS

This application is a national stage filing under 35 U.S.C. 371 of PCT/US2018/031548, filed May 8, 2018, which claims the benefit of EP Application No. 17170973.6, filed May 15, 2017, the disclosures of each of which re incorporated by reference herein in their entireties.

FIELD OF THE INVENTION

The invention relates to a dental adhesive composition comprising a mixture of silanes.

The dental adhesive composition is in particular useful for adhesively fixing dental restorations based on lithium disilicate and other glass ceramic materials to dental surfaces.

BACKGROUND

Besides other materials glass ceramic materials are often used for producing dental restorations.

In order to bond a e.g. methacrylate based formulation to etchable glass ceramic or ceramic materials, either for cementation or repair purposes, typically the surface of the ceramic or glass ceramic material has to be etched with e.g. hydrofluoric acid to create a retention pattern on the surface.

Then, typically a solution of a silane coupling agent dissolved in an organic solvent is applied to the etched surface to create methacrylate functions on the ceramic or glass ceramic material surface. A commercially available product is e.g. ESPE™ Sil (3M Oral Care).

In order to react with the glass ceramic surface, the methoxy groups of the silane coupling agent need to hydrolyze first to form Si—OH groups which can then condensate with the Si—OH groups on the ceramic surface.

If pre-hydrolyzed silanes were used, this surface reaction can be improved (U.S. Pat. No. 4,673,354; Culler). A commercially available product is e.g. RelyX™ Ceramic Primer (3M Oral Care).

Available are also so-called universal primers which contain additional methacrylate functionalized components that can react with other substrates including noble metals and high strength ceramics like zirconia and alumina.

Universal primer compositions often contain phosphorylated methacrylates like 2-methacryloxy ethyl phosphate (MEP) or 10-methacryloxy decyl phosphate (MDP).

In order to further improve the adhesion to noble metals, the addition of various kinds of sulfur containing components is suggested.

U.S. Pat. No. 8,029,613 B2 (Tanaka et al.) describes a one pack type dental adhesive composition comprising a silane coupling agent, a strong acid compound, water and a volatile organic solvent.

U.S. Pat. No. 4,673,354 (Culler) describes a method of priming a dental material using a liquid layer of acidic, non-hazy silanol priming solution containing substantially fully hydrolyzed organofunctional silanol, water and volatile alcohol or ketone solvent.

U.S. Pat. No. 7,776,936 B2 (Tanaka) describes a one pack type dental adhesive composition comprising a silane coupling agent, an acidic group-containing polymerizable monomer and a sulfur atom-containing polymerizable monomer.

JP 2008-001624 (Kuraray) describes a one-pack type adhesive composition for dentistry containing a silane coupling agent having a specific polymerizable group, an acidic group-containing polymerizable monomer, a primary alcohol and water.

U.S. Pat. No. 8,211,956 B2 (Bock et al.) describes an adhesion-promotor composition for the adhesive joining of metallic or ceramic dental materials to radically curing dental materials, wherein the adhesion-promoter composition contains an alkoxysilane monomer, a phosphoric acid ester monomer, a sulfur-containing monomer and an organic solvent.

U.S. Pat. No. 8,710,115 B2 (Thalacker et al.) describes a dental composition comprising an ethylenically unsaturated acidic compound, water, a functionalized silane, an initiator, optionally a sensitizing agent, a non-surface treated filler.

JP 2006-0171795 (Kuraray) describes a one-pack type adhesive composition for dental use containing (a) a silane coupling agent with a specific polymerizable group, (b) an acidic group-containing polymerizable monomer, (c) a primary alcohol and (d) water in an amount of 0.005 to 0.5 wt. %.

US 2016/0022549 A1 (Catel et al.) relates to a primer formulation which contains at least one alkoxysilane monomer, at least one polydrogen fluoride salt, an organic solvent and water, preferably in an amount of 40 to 75 wt. %.

However, there is still room for improvement especially with regard to the requirements to be fulfilled with respect to modern dental materials.

SUMMARY

In particular, it would be desirable to have a composition which can be prepared easily, is easy to use and shows good adhesion to surfaces of dental restorative materials, in particular dental restorative materials being based on feldspathic glass ceramic and/or lithium disilicate.

In one embodiment the present invention features a dental adhesive composition as described in the claims and the present text comprising
ethylenically unsaturated component(s) with acidic moiety,
ethylenically unsaturated component(s) without acidic moiety,
water,
sensitizing agent(s),
reducing agent(s),
optionally filler(s),
a silane composition comprising
(meth)acrylate functional silane(s), and
amino functional silane(s).

In another embodiment, the invention relates to a process of producing the dental composition as described in the claims and the present text.

The invention also relates to a kit of parts and a packaging device containing the dental adhesive composition described in the present text and the claims.

Moreover, the invention features a method of using the dental adhesive composition as described in the present text and the claims for adhesively fixing a dental restoration to a dental surface.

Described is also the use of a silane composition comprising (meth)acrylate functional silane(s) and amino functional silane(s) as described in the present text and the claims for improving the adhesion of a dental adhesive composition to feldspathic glass ceramic or lithium disilicate ceramic Unless defined differently, for this description the following terms shall have the given meaning:

A "dental composition" or a "composition for dental use" or a "composition to be used in the dental field" is any composition which can and is to be used in the dental field. In this respect the composition should be not detrimental to the patients' health and thus free of hazardous and toxic components being able to migrate out of the composition.

Dental compositions are typically hardenable compositions, which can be hardened at ambient conditions, including a temperature range from about 15 to 50° C. or from about 20 to 40° C. within a time frame of about 30 min or 20 min or 10 min. Higher temperatures are not recommended as they might cause pain to the patient and may be detrimental to the patient's health.

Dental compositions are typically provided to the practitioner in comparable small volumes, that is volumes in the range from about 0.1 to about 100 ml or from about 0.5 to about 50 ml or from about 1 to about 30 ml. Thus, the storage volume of useful packaging devices is within these ranges.

If the packaging device is intended for a single use only, the volume is typically in a range of 0.03 to 2 ml or 0.06 to 1 ml or 0.08 to 0.3 ml.

A "polymerizable component" is any component which can be cured or solidified e.g. by heating to cause polymerization or chemical crosslinking, or e.g. by radiation-induced polymerization or crosslinking, or e.g. using a redox initiator or by any other radical forming process. A radically polymerizable component may contain only one, two, three or more radically polymerizable groups. Typical examples of radically polymerizable groups include unsaturated carbon groups, such as a vinyl group being present e.g. in a (methyl)acrylate group.

A "monomer" is any chemical substance which can be characterized by a chemical formula, bearing radically polymerizable unsaturated groups (including (meth)acrylate groups) which can be polymerized to oligomers or polymers thereby increasing the molecular weight. The molecular weight of monomers can usually simply be calculated based on the chemical formula given.

As used herein, "(meth)acryl" is a shorthand term referring to "acryl" and/or "methacryl". For example, a "(meth) acryloxy" group is a shorthand term referring to either an acryloxy group (i. e., $CH_2=CH—C(O)—O—$) and/or a methacryloxy group (i. e., $CH_2=C(CH_3)—C(O)—O—$).

An "ethylenically unsaturated acidic compound" is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, phosphonic acid residues or sulfonic acid residues, such as —$SO_3H$.

A "solvent" means a liquid which is able to at least partially disperse or dissolve a component at ambient conditions (e.g. 23° C.). A solvent typically has a viscosity below about 5 or below about 1 or below about 0.1 Pa*s.

As used herein, "hardening" or "curing" a composition are used interchangeably and refer to polymerization and/or crosslinking reactions including, for example, photopolymerization reactions and chemical polymerization techniques (e. g., ionic reactions or chemical reactions forming radicals effective to polymerize ethylenically unsaturated compounds) involving one or more materials included in the composition.

A "derivative" or "structural analogue" is a chemical compound showing a chemical structure closely related to the corresponding reference compound and containing all featured structural elements of the corresponding reference compound but having small modifications like bearing additional chemical groups like e.g. alkyl moieties, Br, Cl, or F or not bearing chemical groups like e.g. alkyl moieties in comparison to the corresponding reference compound. That is, a derivative is a structural analogue of the reference compound. A derivative of a chemical compound is a compound comprising the chemical structure of said chemical compound.

As used herein, a "dental surface" refers to tooth structures (e. g., enamel, dentin, and cementum) and bone.

A "self-etching composition" refers to a composition which bonds to a dental surface without pre-treating the dental surface with an etchant. Preferably, a self-etching composition can also function as a self-adhesive primer wherein no separate etchant or primer is used.

A "self-adhesive composition" refers to a composition that is capable of bonding to a dental surface without pre-treating the dental surface with a primer or bonding agent. Preferably, a self-adhesive composition is also a self-etching composition wherein no separate etchant is used.

An "untreated dental surface" refers to a tooth or bone surface that has not been treated with an etchant, primer, or bonding agent prior to application of a self-etching adhesive or a self-adhesive composition.

An "unetched" dental surface refers to a tooth or bone surface that has not been treated with an etchant prior to application of a self-etching adhesive or a self-adhesive composition.

"In-situ silanization" is to be understood as a reaction between a non-surface treated filler with a functionalised silane compound to obtain a filler, the surface of which is partially or wholly surface-treated without the need to isolate the filler from the reaction mixture. Examples for coupling agents and methods for applying them to a filler surface can be found in E. P. Plueddemann, Silane Coupling Agents, 2nd Ed., Plenum Press, New York 1991.

A "functionalised silane compound" is a silane compound bearing one or more moieties, which are able to undergo chemical reactions beyond condensation with OH— moieties of other silanes or on the surface of a filler. Examples of functionalised silane compounds include amino or (meth) acrylate functionalised silanes, like 3-aminopropyl trimethoxysilane or 3-(meth)acryloxypropyl trimethoxysilane.

A "non-surface treated filler" in the context of the invention is a filler having a surface which has not been exposed to reactive substances resulting in a modification of the surface of the filler to make the filler more compatible with other components of the composition.

"Ambient conditions" mean the conditions which the inventive solution is usually subjected to during storage and handling. Ambient conditions may, for example, be a pressure of 900 to 1100 mbar, a temperature of 10 to 40° C. and a relative humidity of 10 to 100%. In the laboratory, ambient conditions are adjusted to 20 to 25° C. and 1000 to 1025 mbar.

A composition is "essentially or substantially free of" a certain component, if the composition does not contain said component as an essential feature. Thus, said component is not wilfully added to the composition either as such or in combination with other components or ingredient of other components. A composition being essentially free of a certain component usually does not contain that component at all. However, sometimes the presence of a small amount of the said component is not avoidable e.g. due to impurities contained in the raw materials used.

As used herein, "a", "an", "the", "at least one" and "one or more" are used interchangeably. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

Unless otherwise indicated, all numbers expressing quantities of ingredients, measurement of physical properties such as described below and so forth used in the specification and claims are to be understood as being modified in all instances by the term "about".

The terms "comprise" or "contain" and variations thereof do not have a limiting meaning where these terms appear in the description and claims. The term "comprise" shall include also the terms "consist essentially of" and "consist of".

DETAILED DESCRIPTION

The dental adhesive composition described in the present text has a couple of advantages. The dental composition can be prepared easily, e.g. by simply mixing the components of the composition in a one-pot procedure.

The dental composition shows good adhesion not only to dental surfaces, but also to the surface of dental restoration made from ceramic or glass ceramic materials.

In particular it was found that providing a composition as described in the present text, to which a mixture of an amino functional silane and a (meth)acrylate functional silane has been added, the bond strength of such a composition to the surface of feldspathic glass ceramic and lithium disilicate can be improved.

In certain embodiments the composition described in the present text can be characterized by the following properties alone or in combination:
Viscosity: 0.01 to 3 Pa*s at 23° C.;
pH value: 1 to 5 if determined with a pH sensitive paper,
Shear bond strength to hydrofluoric acid etched lithium disilicate and feldspathic dental ceramics of at least 20 MPa according to DIN EN ISO 29022 (2013-09).

If desired, the respective properties can be determined as described in the example section.

The dental adhesive composition described in the present text comprises one or more ethylenically unsaturated component(s) with acidic moiety as Component (A).

The nature and structure of Component (A) is not particularly limited unless the desired result cannot be achieved.

Examples of the acidic moiety include carboxylic acid residues, phosphoric acid residues, phosphonic acid residues or sulfonic acid residues.

In one embodiment, the polymerizable component having an acidic moiety can be represented by the following formula $A_n BC_m$ B being a backbone group, such as (i) linear or branched $C_1$ to $C_{12}$ alkyl, optionally substituted with OH, (ii) $C_6$ to $C_{12}$ aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, A being an ethylenically unsaturated group attached to the backbone group, such as a (meth)acryl moiety, C being an acidic group attached to the backbone group, with m, n=1, 2, 3, 4, 5 or 6, wherein the acidic group comprises one or more carboxylic acid residues, such as —COOH or —CO—O—CO—, phosphoric acid residues, such as —O—P(O)(OH)OH, phosphonic acid residues or sulphonic acid residues, such as —SO₃H.

Specific examples of ethylenically unsaturated acidic compounds include, but are not limited to glycerol phosphate mono(meth)acrylates, glycerol phosphate di(meth)acrylates, hydroxyethyl (meth)acrylate phosphates, bis glycerol phosphate di(meth)acrylates, bis((meth)acryloxyethyl) phosphate, ((meth)acryloxypropyl) phosphate, bis((meth)acryloxypropyl) phosphate, bis((meth)acryloxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, di or tri(meth)acrylated citric acid, poly(meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly(meth)acrylated polysulfonate, poly(meth)acrylated polyboric acid, and the like.

The reaction products of (meth)acrylic acid with alkane diols (e.g. $C_2$ to $C_{20}$ or $C_2$ to $C_{12}$ or $C_6$ to $C_{10}$) and phosphorous oxide were found to be suitable as well.

Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example in US 2004/0206932 A1 (Abuelyaman); AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Fuchigami et al.) and EP 1 051 961 A1 (Hino et al.).

Typical compositions also include an ethylenically unsaturated acidic compound with at least one phosphoric acid group (e.g. P—OH moiety).

Examples of preferred phosphoric acid group-containing polymerizable monomer include 6-(meth)acryloxyhexyl dihydrogenphosphate, 7-(meth)acryloxyheptyl dihydrogenphosphate, 8-(meth)acryloxyoctyl dihydrogenphosphate, 9-(meth)acryloxynonyl dihydrogenphosphate, 10-(meth)acryloxydecyl dihydrogenphosphate, 11-(meth)acryloxyundecyl dihydrogenphosphate, 12-(meth)acryloxydodecyl dihydrogenphosphate, 16-(meth)acryloxyhexadecyl dihydrogenphosphate, 20-(meth)acryloxyeicosyl dihydrogenphosphate, bis[6-(meth)acryloxyhexyl]hydrogenphosphate, bis[8-(meth)acryloxyoctyl]hydrogenphosphate, bis[9-(meth)acryloxynonyl]hydrogenphosphate, bis[10-(meth)acryloxydecyl]hydrogenphosphate, 1,3-di(meth)acryloxypropyl dihydrogenphosphate, 2-(meth)acryloxyethylphenyl hydrogenphosphate, 2-(meth)acryloxyethyl-2-bromoethyl hydrogenphosphate, (5-methacryloxy)pentyl-3-phosphonopropionate, (6-methacryloxy)hexyl-3-phosphonopropionate, (10-methacryloxy)decyl-3-phosphonopropionate, (6-methacryloxy)hexyl-3-phosphonoacetate, (10-methacryloxy)-decyl-3-phosphonoacetate, 2-methacryloxyethyl (4-methoxyphenyl) hydrogenphosphate and 2-methacryloxypropyl (4-methoxyphenyl) hydrogenphosphate and mixtures thereof.

Component (A) is typically present in the following amount(s):
Lower limit: at least 1 or at least 2 or at least 3 wt. %;
Upper limit: utmost 20 or utmost 25 or utmost 30 wt. %;
Range: 1 to 30 or 2 to 25 or 3 to 20 wt. %;
wt. % with respect to the whole amount of the composition.

The dental adhesive composition described in the present text comprises one or more ethylenically unsaturated component(s) without acidic moiety as Component (B).

The nature and structure of Component (B) is not particularly limited unless the desired result cannot be achieved.

The ethylenically unsaturated component(s) without acidic moiety(s) is typically a free-radically polymerizable material, including ethylenically unsaturated monomer, monomers or oligomers or polymers.

Suitable polymerizable component(s) without acidic moiety(s) can be characterized by the following formula:

$A_n BA_m$ with A being an ethylenically unsaturated group attached to backbone B, such as a (meth)acryl moiety,
B being selected from (i) linear or branched $C_1$ to $C_{12}$ alkyl, optionally substituted with other functional groups (e.g. halogenides (including Cl, Br, I), OH or mixtures thereof) (ii) $C_6$ to $C_{12}$ aryl, optionally substituted with other functional groups (e.g. halogenides, OH or mixtures thereof), or (iii) organic group having 4 to 20 carbon atoms bonded to one another by one or more ether, ester, amide, urethane, carbonyl and/or sulfonyl linkages,
m, n being independently selected from 0, 1, 2, 3, 4, 5 or 6 with the proviso that n+m is greater 0, that is that at least one A group is present.

Such polymerizable materials include mono-, di- or polyacrylates and methacrylates such as methyl acrylate, methyl methacrylate, ethyl (meth)acrylate, isopropyl (meth)acrylate, n-hexyl (meth)acrylate, stearyl (meth)acrylate, allyl (meth)acrylate, glycerol di(meth)acrylate, the diurethane dimethacrylate called UDMA (mixture of isomers, e.g. Röhm Plex 6661-0) being the reaction product of 2-hydroxyethyl methacrylate (HEMA) and 2,2,4-trimethylhexamethylene diisocyanate (TMDI), glycerol tri(meth)acrylate, ethyleneglycol di(meth)acrylate, diethyleneglycol di(meth)acrylate, triethyleneglycol di(meth)acrylate, 1,3-propanediol diacrylate, 1,3-propanediol dimethacrylate, trimethylolpropane tri(meth)acrylate, 1,2,4-butanetriol tri(meth)acrylate, 1,4-cyclohexanediol di(meth)acrylate, pentaerythritol tri(meth)acrylate, pentaerythritol tetraacrylate, pentaerythritol tetramethacrylate, sorbitol hexa(meth)acrylate, bis[1-(2-(meth)acryloxy)]-p-ethoxyphenyldimethylmethane, bis[1-(3-methacryloxy-2-hydroxy)]-p-propoxyphenyldimethylmethane (BisGMA), and tri shydroxyethylisocyanurate trimethacrylate; the bis-acrylates and bis-methacrylates of polyethylene glycols of molecular weight 200-500, copolymerizable mixtures of acrylated monomers (see e.g. U.S. Pat. No. 4,652,274), and acrylated oligomers (see e.g. U.S. Pat. No. 4,642,126); and vinyl compounds such as styrene, diallyl phthalate, divinyl succinate, divinyl adipate and divinylphthalate; polyfunctional (meth)acrylates comprising urethane, urea or amide groups. Mixtures of two or more of these free radically polymerizable materials can be used if desired.

Further polymerizable components which may be present include di(meth)acrylates of ethoxylated bis-phenol A, for example 2,2'-bis(4-(meth)acryl-oxytetraethoxyphenyl)propanes, 2,2'-bis(4-(meth)acryloxytriethoxyphenyl)propanes, 2,2'-bis(4-(meth)acryloxydiethoxyphenyl)propanes, urethane (meth)acrylates and (meth)acrylamides. The monomers used can furthermore be esters of [alpha]-cyanoacrylic acid, crotonic acid, cinnamic acid and sorbic acid.

It is also possible to use the methacrylic esters mentioned in EP 0 235 826 A1 (Schmitt et al.), such as bis[3[4]-methacryl-oxymethyl-8(9)-tricyclo[5.2.1.0$^{2,6}$]decylmethyl triglycolate. Suitable are 2,2-bis-4-(3-methacryloxypropoxy) phenylpropane, urethane (meth)acrylates and di(meth)acrylates of bishydroxymethyltricyclo-(5.2.1.0$^{2,6}$)decane.

Further examples for polymerizable component(s) without an acidic moiety are the dimethycrylate and the diacrylate derived from tricyclodecane-dimethanol (mixture of isomers) ("T-Acrylat", "T-Methacrylat"), reaction products of tricyclodecane-dimethanol with isocyanatoethyl (meth)acrylate, reaction products of tricyclodecane-diisocyanate with hydroxyethyl (meth)acrylate or hydroxypropyl (meth)acrylate.

These ethylenically unsaturated monomers can be employed in the dental composition(s) either alone or in combination with the other ethylenically unsaturated monomers. In addition or besides those components, other hardenable components which can be added include oligomeric or polymeric compounds, such as polyester (meth)acrylates, polyether (meth)acrylates, polycarbonate (meth)acrylates and polyurethane (meth)acrylates. The molecular weight of these compounds is typically less than 20,000 g/mol, particularly less than 15,000 g/mol and in particular less than 10,000 g/mol.

Polymerizable monomers comprising a hydroxyl moiety and/or a 1,3-diketo moiety can also be added. Suitable compounds include 2-hydroxyethyl methacrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 10-hydroxydecyl (meth)acrylate, dialkylene glycol mono(meth)acrylate, for example, diethylene glycol mono(meth)acrylate, triethylene glycol mono(meth)acrylate, tetraethylene glycol mono(meth)acrylate, polyethylene glycol mono(meth)acrylate, dipropylene glycol mono(meth)acrylate, polypropylene glycol mono(meth)acrylate, and further 1,2- or 1,3- and 2,3-dihydroxypropyl (meth)acrylate, 2-hydroxypropyl-1,3-di(meth)acrylate, 3-hydroxypropyl-1, 2-di(meth)acrylate, N-(meth)acryloyl-1,2-dihydroxypropylamine, N-(meth)acryloyl-1,3-dihydroxypropylamine, adducts of phenol and glycidyl (meth)acrylate, for example, 1-phenoxy-2-hydroxypropyl (meth)acrylate, 1-naphthoxy- 2-hydroxypropyl (meth)acrylate, bisphenol A diglycidyl (meth)acrylate and the like. 2-Hydroxyethyl (meth)acrylate, 2-hydroxypropyl (meth)acrylate and 2,3-dihydroxypropyl (meth)acrylate are sometimes preferred.

Component (B) is typically present in the following amount(s):
Lower limit: at least 10 or at least 20 or at least 30 wt. %;
Upper limit: utmost 60 or utmost 70 or utmost 80 wt. %;
Range: 10 to 80 or 20 to 70 or 30 to 60 wt. %;
wt. % with respect to the whole amount of the composition.

The dental adhesive composition described in the present text comprises water as Component (C).

Water is typically provided in the form of de-ionized water.

Water is typically present in the following amount(s):
Lower limit: at least 1 or at least 3 or at least 5 or at least 8 wt. %;
Upper limit: utmost 15 or utmost 20 or utmost 30 wt. %;
Range: 1 to 30 or 3 to 20 or 5 to 15 wt. %;
wt. % with respect to the whole amount of the composition.

The dental adhesive composition described in the present text comprises one or more sensitizing agents as Component (D).

The nature and structure of the sensitizing agent is not particularly limited unless the intended purpose is not negatively affected.

Suitable sensitizing agent for free radical polymerization are generally known to the person skilled in the art dealing with dental materials.

As the sensitizing agent, those which can polymerize the polymerizable monomer(s) by the action of a visible light having a wavelength of from 390 nm to 830 nm are preferred.

Suitable sensitizing agents often contain an alpha di-keto moiety, an anthraquinone moiety, a thioxanthone moiety or benzoin moiety.

Examples of sensitizing agents include camphorquinone, 1-phenyl propane-1,2-dione, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4,'-bisdiethylaminobenzophenone.

Component (D) is typically present in the following amount(s):
Lower limit: at least 0.1 or at least 0.3 or at least 0.6 wt. %;
Upper limit: utmost 2 or utmost 3 or utmost 4 wt. %;
Range: 0.1 to 4 or 0.3 to 3 or 0.6 to 2 wt. %;
wt. % with respect to the whole amount of the composition.

The dental adhesive composition described in the present text comprises one or more reducing agents as Component (E). As reducing agent amines, in particular secondary and tertiary amines can be used.

Suitable examples include triethanolamine, diethanolamine, methyl diethanolamine, 2-dimethylaminoethyl (meth)acrylate, 3-dim ethylaminopropyl (meth)acrylate, 4-dimethylaminobutyl (meth)acrylate, 6-dimethylaminohexyl (meth)acrylate, 10-dimethylaminodecyl (meth)acrylate, 4-dimethylaminophenetyl alcohol, 4-diethylaminophenetyl alcohol, 4-dipropylaminophenetyl alcohol, N,N-di(2-hydroxyethyl)-p-toluidine, N,N-di(2-hydroxypropyl)-p-toluidine, N,N-dimethyl-p-toluidine, N,N-dipropyl-p-toluidine, N,N-diethyl-p-toluidine, N,N-diethoxyethyl-p-toluidine, N,N-dibutoxyethyl-p-toluidine, N,N-di(polyoxyethylene)oxyethyl-p-toluidine,
hexamethylenediamine, a dimethylamine aqueous solution, pentamethylenediamine, diethylamine, ethylenediamine, 2-aminoethanol, triethylamine and 2-dimethylaminoethanol.

In particular the following amines were found to be useful: N,N-dimethylaminoethyl methacrylate, ethyl 4-dimethylaminobenzoate, methyl 4-dimethylaminobenzoate, triethanolamine, N,N-dimethyl-p-toluidine, N,N-di(2-hydroxyethyl)-p-toluidine, and isoamyl 4-dimethylaminobenzoate.

Moreover, ternary photopolymerization initiating systems comprising a sensitizer, an electron donor and an onium salt as described in U.S. Pat. No. 6,187,833 (Oxman et al), U.S. Pat. No. 6,025,406 (Oxman et al.), U.S. Pat. No. 6,043,295 (Oxman et al.), U.S. Pat. No. 5,998,495 (Oxman et al), U.S. Pat. No. 6,084,004 (Weinmann et al.) and US 2003/0166737 A1 (Dede et al.) can be used, too.

Other reducing agents, like sodium sulfinate derivatives and organometallic compounds can be used, as well. These compounds may be used singly or in admixture.

Specific examples of sulfinic acid components include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid.

Particularly suitable sulfinic acid component are sodium toluene sulfinate or sodium benzene sulfinate and their hydrates.

It is also possible to use a quadruple photopolymerization initiating system comprising two different sensitizers and two different reducing agents.

Component (E) is typically present in the following amount(s):
Lower limit: at least 0.1 or at least 0.3 or at least 0.6 wt. %;
Upper limit: utmost 2 or utmost 3 or utmost 4 wt. %;
Range: 0.1 to 4 or 0.3 to 3 or 0.6 to 2 wt. %;
wt. % with respect to the whole amount of the composition.

The dental adhesive composition described in the present text comprises a silane composition as Component (F).

The silane composition comprises (meth)acrylate functional silane(s) and amino functional silane(s).

The silane composition comprises one or more (meth) acrylate functional silanes as
Component (F1).

The nature and structure of the (meth)acrylate functional silanes is not particularly limited unless the intended purpose is not negatively affected.

The functionalized silane compound according to component (F1) is usually an alkoxy silane, preferably a trialkoxy silane comprising a (meth)acrylate group and at least one group that can hydrolyse with water.

Typical embodiments can be characterized by the following formula:

$A_m\text{—}B\text{—}Si(R^1)_n(OR^2)_{3-n}$ with A comprising a (meth)acryl moiety,
B comprising a spacer group, such as (i) linear or branched $C_1$ to $C_{12}$ alkyl, (ii) $C_6$ to $C_{12}$ aryl, (iii) organic group having 2 to 20 carbon atoms bonded to one another by one or more ether, thioether, ester, thioester, thiocarbonyl, amide, urethane, carbonyl and/or sulfonyl linkages, $R^1$ comprising an alkyl group (e.g. $C_1$ to $C_6$) or an aryl group (e.g. $C_6$ to $C_{12}$), and $R^2$ comprising an alkyl group (e.g. $C_1$ to $C_6$), with m=1, 2, 3 or 4 and n=0, 1 or 2.

Examples of (meth)acrylate functionalized trialkoxy silanes include, but are not limited to 3-(meth)acryloxypropyl trimethoxysilane, 3-(meth)acryloxypropyl triethoxysilane, 3-(meth)acryloxypropyl tris(methoxyethoxy)silane, 3-(meth)acryloxy-propenyl trimethoxysilane, (meth)acryloxyethyldimethyl(3-trimethoxysilylpropyl)-ammonium chloride, N-(3-(meth)acryloxy-2-hydroxypropyl)-3-aminopropyltriethoxy-silane, O-((meth)acryloxyethyl)-N-(triethoxysilylpropyl)urethane, (meth)acryloxymethyl trimethoxysilane, (meth)acryloxymethyl triethoxysilane, (meth)acryloxymethyl methyldimethoxysilane, (meth)acryloxymethyl methyl diethoxysilane, (meth)acryloxyoctyl trimethoxysilane, [(meth)acryloxymethyl]phenethyl trimethoxysilane, O-[(meth)acryloxyethyl]-N-(triethoxysilylpropyl)carbamate, (meth)acryloxypropyl triisopropoxysilane, (meth)acryloxypropyl methyldimethoxysilane, (meth)acryloxypropyl methyldiethoxysilane, 3-(meth)acryloxypropyl dimethylmethoxysilane, 3-(meth)acryloxypropyl dimethylethoxysilane, (meth) acryloxymethyl dimethylmethoxysilane, (meth) acryloxymethyl dimethylethoxysilane, oligomeric hydrolysate of 3-(meth)acryloxypropyl trimethoxysilane, oligomeric hydrolysate of 3-(meth)acryloxypropyl triethoxysilane. These organosilane compounds may be used alone or in combination. The molecular weight of this component is typically within a range from 200 to 400 g/mol.

In case a hydrolysis and/or condensation takes place, the molecular weight of the respective oligomeric hydrolysate/condensate may be in a range of 1,000 to 2,000 g/mol.

Component (F1) is typically present in the following amount(s):

Lower limit: at least 0.2 or at least 0.5 or at least 1.0 wt. %;

Upper limit: utmost 4 or utmost 5 or utmost 6 wt. %;

Range: 0.2 to 6 or 0.5 to 5 or 1 to 4 wt. %;

wt. % with respect to the whole amount of the composition.

The silane composition comprises one or more amino functional silanes as Component (F2).

The nature and structure of the amino functional silanes is not particularly limited unless the intended purpose is not negatively affected. However, primary and secondary amino functional silane are typically preferred.

According to one embodiment, the amino functional silane is characterized by the following formula:

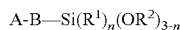

$$A\text{-}B\text{—}Si(R^1)_n(OR^2)_{3-n}$$

with A comprising an amino moiety,

B comprising a spacer group, such as (i) linear or branched $C_1$ to $C_{12}$ alkyl, (ii) $C_6$ to $C_{12}$ aryl, (iii) organic group having 2 to 20 carbon atoms bonded to one another by one or more ether, thioether, ester, thioester, thiocarbonyl, amide, urethane, carbonyl and/or sulfonyl linkages, $R^1$ comprising an alkyl group (e.g. $C_1$ to $C_6$) or an aryl group (e.g. $C_6$ to $C_{12}$), and $R^2$ comprising an alkyl group (e.g. $C_1$ to $C_6$), with n=0, 1 or 2.

Specific examples of amino functional silanes include 3-aminopropyl trimethoxysilane, 3-aminopropyl triethoxysilane, N-(2-aminoethyl)-3-aminopropyl trimethoxysilane, N-(2-aminoethyl)-3-aminopropyl triethoxysilane, N-cyclohexyl-3-aminopropyl trimethoxysilane, N-cyclohexyl-3-aminopropyl trimethoxysilane, 4-aminobutyl trimethoxysilane, 4-aminobutyl triethoxysilane, 4-amino-3,3-dimethylbutyl trimethoxysilane, 11-aminoundecyl triethoxysilane, 3-aminopropyl silanetriol, 4-amino-3,3-dimethylbutyl methyldimethoxysilane, 3-aminopropyl methyldimethoxysilane, 1-amino-2-(dimethylethoxysilyl)propane, 3-aminopropyl diisopropylethoxysilane, 3-aminopropyl dimethylethoxysilane, (aminoethylaminomethyl)phenethyl trimethoxysilane, N-(6-aminohexyl)aminomethyl triethoxysilane, N-(6-aminohexyl)aminopropyl trimethoxysilane, N-(2-aminoethyl)-11-aminoundecyl trimethoxysilane, N-3-[amino(polypropylenoxy)]aminopropyl trimethoxysilane, N-(2-N-benzylaminoethyl)-3-aminopropyl trimethoxysilane, N-(2-aminoethyl)-3-aminopropyl silanetriol, N-(2-aminoethyl)-3-aminopropyl trimethoxysilane-propyl trimethoxysilane oligomers, N-(2-aminoethyl)-3-aminopropyl methyldimethoxysilane, N-(2-aminoethyl)-3-aminopropyl methyldiethoxysilane, N-(2-aminoethyl)-3-aminoisobutyl dimethylmethoxysilane, (3-trimethoxysilylpropyl)diethylenetriamine, 3-(N-allylamino)propyl trimethoxysilane, n-butylaminopropyl trimethoxysilane, t-butylaminopropyl trimethoxysilane, (N-cyclohexylaminomethyl) methyldiethoxysilane, (N-cyclohexylaminomethyl) triethoxysilane, (3-(N-ethylamino) isobutyl) methyldiethoxysilane, (3-N-(ethylamino)isobutyl) trimethoxysilane, N-methylaminopropyl methyldimethoxysilane, N-methylaminopropyl trimethoxysilane, (N-phenylaminomethyl) methyldimethoxysilane, N-phenylaminomethyl triethoxysilane, N-phenylaminopropyl trimethoxysilane, 1-[3-(2-aminoethyl)-3-aminoisobutyl]-1,1,3,3,3-pentaethoxy-1,3-disilapropane, bis(methyldiethoxysilylpropyl)amine, bis(3-triethoxysilylpropyl)amine, 1,11-bis(trimethoxysilyl)-4-oxa-8-azaundecan-6-ol, bis(3-trimethoxysilylpropyl)amine, N,N'-bis[(3-trimethoxysilyl)propyl]ethylenediamine and mixtures thereof. Primary amino functional silanes are sometimes preferred.

Compared to alkyl-substituted amino functional silanes, non alkyl-substituted amino functional silanes were found to have better performance in the intended application.

Examples of those include 3-aminopropyl trimethoxysilane, 3-aminopropyl triethoxysilane, 4-aminobutyl trimethoxysilane, 4-aminobutyl triethoxysilane, 4-amino-3, 3-dimethylbutyl trimethoxysilane, 11-aminoundecyl triethoxysilane, 3-aminopropyl silanetriol, 4-amino-3,3-dimethylbutyl methyldimethoxysilane, 3-aminopropyl methyldimethoxysilane, 1-amino-2-(dimethylethoxysilyl) propane, 3-aminopropyl diisopropylethoxysilane, 3-aminopropyl dimethylethoxysilane, and mixtures thereof.

The molecular weight of this component is typically within a range of 160 to 500 g/mol.

In case a hydrolysis and/or condensation takes place, the molecular weight of the respective oligomeric hydrolysate/condensate may be in a range of 1,000 to 2,000 g/mol.

Component (F2) is typically present in the following amount(s):

Lower limit: at least 0.2 or at least 0.5 or at least 1 wt. %;

Upper limit: utmost 2 or utmost 3 or utmost 4 wt. %;

Range: 0.2 to 4 or 0.5 to 3 or 1 to 2 wt. %;

wt. % with respect to the whole amount of the composition.

The (meth)acrylate functional silane(s) is typically used in equal proportion or in excess with respect to weight over the amino functional silane(s).

A ratio where the amount of (meth)acrylate functional silane with respect to weight to the amount of amino functional silane with respect to weight does not exceed about 5 or about 3 or about 2 was found to be particularly useful to obtain good adhesion.

On the other hand, if the amount of (meth)acrylate functional silane with respect to the total silane content is too low, the adhesion to glass ceramic surfaces might be reduced.

According to one embodiment, the amino functional silane is used in an amount to keep the pH of the dental adhesive composition below 5 or 4 or 3.

If the pH is outside this range, uncontrolled condensation and/or precipitation of the silanes might occur.

The dental adhesive composition described in the present text may comprise one or more fillers as Component (G).

Fillers may be selected from one or more of a wide variety of materials suitable for incorporation in compositions used for dental applications, such as fillers currently used in dental restorative compositions, and the like.

The filler(s) which may be used in the compositions of the present text is preferably finely divided. The filler(s) can have a unimodial or polymodial (e.g., bimodal) particle size distribution. Typically, the maximum particle size (the largest dimension of a particle, generally, the diameter) of the filler(s) is less than 20 µm, more typically less than 10 µm, and most preferably less than 5 µm. Typically, the average particle size of the filler(s) is less than 0.1 µm, and more typically less than 0.075 µm.

The compositions may include a filer comprising an inorganic material. It can also be a crosslinked organic material that is insoluble in the resin system, and is optionally filled with inorganic filler. The filler(s) should in be nontoxic and suitable for use in the mouth or a patient. The filler(s) can be radiopaque or radiolucent. The filler typically is substantially insoluble in water.

Examples of suitable inorganic fillers are naturally occurring or synthetic materials including, but not limited to: quartz; nitrides (e.g., silicon nitride); glasses derived from, for example, Zr, Sr, Ce, Sb, Sn, Ba, Zn, and Al; feldspar; borosilicate glass; kaolin; talc; titania; low Mohs hardness fillers such as those described in U.S. Pat. No. 4,695,251 (Randklev); and submicron silica particles (e.g., pyrogenic silicas such as those available under the trade designations AEROSIL, including "OX 50," "130," "150" and "200" silicas from Evonik Industries AG, Essen, Germany, and CAB-O-SIL M5 silica from Cabot Corp., Tuscola, Ill.). Examples of suitable organic filler particles include filled or unfilled pulverized polycarbonates, polyepoxides, and the like.

Suitable non-acid-reactive filler particles include quartz, submicron silica, and non-vitreous microparticles of the type described in U.S. Pat. No. 4,503,169 (Randklev). Mixtures of these non-acid-reactive fillers are also contemplated, as well as combination fillers made from organic and inorganic materials. Silane-treated zirconia-silica (Zr—Si) filler is especially useful in certain embodiments.

Other suitable fillers are disclosed in U.S. Pat. No. 6,387,981 (Zhang et al.); U.S. Pat. No. 6,572,693 (Wu et al.); U.S. Pat. No. 6,730,156 (Windisch); and U.S. Pat. No. 6,899,948 (Zhang); as well as in International Publication No. WO 03/063804 (Wu et al.). Filler components described in these references include nanosized silica particles, nanosized metal oxide particles, and combinations thereof. Nanofillers are also described in U.S. Patent Publication Nos. 2005/0252413 (Kangas et al.); 2005/0252414 (Craig et al.); and 2005/0256223 (Kolb et al.).

The surface of the filler particles can be pre-treated with a coupling agent in order to enhance the bond between the filler and the resin. The use of suitable coupling agents include gamma-methacryloxypropyltrimethoxysilane, gamma-mercaptopropyltriethoxysilane, gamma-aminopropyltrimethoxysilane, and the like. Non-surface treated fillers can be used as well and are sometimes preferred. Fumed or precipitated silica has been found to be particularly useful.

Examples of non-surface treated fillers which can be used include AEROSIL™, including "OX 50," "90", "130", "150", "200", "300", and "380" silicas (Evonik Industries AG, Essen, Germany), and Cab-O-Sil, including "LM-150", "M-5", "H-5", "EH-5" silicas (Cabot Corp., Tuscola, Ill.), and HDK™, including "S13", "V15", "N20", "T30", "T40" silicas (Wacker-Chemie AG, Munich, Germany), and Orisil™, including "200", "300", "380" silicas (Orisil, Lviv, Ukraine).

Further examples of silica fillers according to component (G) include, but are not limited to precipitated silicas such as those available under the brands Sipernat™, Ultrasil™, and Acematt™ (Evonik Industries AG, Essen, Germany), Lo-Vel™ and Hi-Sil™ (PPG Industries, Pittsburgh, Pa.), Zeosil (Rhodia, Paris la Defense, France). Suitable pyrogenic silica fillers can have a specific surface area of 100 to 400 $m^2/g$.

Component (G) is typically present in the following amount(s):
  Lower limit: at least 1 or at least 3 or at least 5 wt. %;
  Upper limit: utmost 20 or utmost 30 or utmost 40 wt. %;
  Range: 1 to 40 or 3 to 30 or 5 to 20 wt. %;
wt. % with respect to the whole amount of the composition.

The dental adhesive composition described in the present text may also comprise one or more solvent(s) as component (H).

Adding solvent(s) or co-solvent(s) may help to adjust the viscosity and consistency of the composition.

Examples of solvents according to component (F) include, but are not limited to linear, branched or cyclic, saturated or unsaturated alcohols, ketones, esters or mixtures of two or more of said type of solvents with 2 to 10 C atoms. Preferred alcoholic solvents include methanol, ethanol, isopropanol and n-propanol.

Other suitable organic solvents are THF, acetone, methylethyl ketone, cyclohexanol, toluene, alkanes and acetic acid alkyl esters, in particular acetic acid ethyl ester.

It is possible to use the above-mentioned solvents alone or as a mixture of two or more of any of these solvents, if the solvent mixtures do not impair the adhesive properties to such an extent that the desired result cannot be obtained.

If present, Component (H) is present in the following amount(s):
  Lower limit: at least 2 or at least 5 or at least 10 wt. %;
  Upper limit: utmost 50 or utmost 30 or utmost 20 wt. %;
  Range: 2 to 50 or 5 to 30 or 10 to 20 wt. %;
wt. % with respect to the whole amount of the composition.

The dental adhesive composition described in the present text may also comprise one or more additive(s) as component (I).

Additives or adjuvants which can be used include inhibitors or retarders, stabilizers, dyes, fluoride release agents, surface tension depressants and wetting aids, antioxidants, and other ingredients well known to those skilled in the art. The amounts and types of each ingredient in the composition should be adjusted to provide the desired physical and handling properties before and after polymerization.

Examples of stabilizers include 2,6-di-tert-butyl-4-methylphenol (butylated hydroxytoluene, BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentylphenyl)-2H-benzotriazole, 2-hydroxy-4-n-octoxybenzophenone, and 2-(2'-hydroxy-5'-methacryl-oxyethylphenyl)-2H-benzotriazole.

Examples of photobleachable colorants include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725. The colour of the compositions of the invention may be additionally imparted by a sensitizing compound.

Examples of fluoride release agents are naturally occuring or synthetic fluoride minerals such as sodium fluoride, fluoride glass such as fluoroaluminosilicate glass, simple and complex inorganic fluoride salts such as potassium zinc fluoride and potassium hexa fluorotitanate, simple and complex organic fluoride salts such as tetraethylammonium tetrafluoroborate or combinations thereof. Particulate fluoride sources can optionally be treated with surface treatment agents.

If present, Component (I) is present in the following amount(s):
Lower limit: at least 0.001 or at least 0.01 or at least 0.02 or at least 0.1 or at least 0.2 wt. %;
Upper limit: utmost 2 or utmost 1 or utmost 0.5 wt. %;
Range: 0.001 to 2 or 0.01 to 2 or 0.02 to 1 or 0.05 to 0.5 wt. %;
wt. % with respect to the whole amount of the composition.

According to one embodiment, the dental adhesive composition of the present text comprises:
ethylenically unsaturated component(s) with acidic moiety: 1 to 30 wt. % or 3 to 20 wt. %,
ethylenically unsaturated component(s) without acidic moiety: 10 to 80 wt. % or 30 to 60 wt. %,
water: 1 to 30 wt. % or 5 to 15 wt. %,
sensitizer(s): 0.1 to 4 wt. % or 0.6 to 2 wt. %,
reducing agent(s): 0.1 to 4 wt. % or 0.6 to 2 wt. %,
non-surface treated filler: 1 to 40 wt. % or 5 to 20 wt. %,
(meth)acrylate functional silane: 0.2 to 6 wt. % or 1 to 4 wt. %,
amino functional silane: 0.2 to 4 wt. % or 1 to 2 wt. %,
solvent(s): 0 to 50 wt. % or 1 to 20 wt. %,
additive(s): 0 to 2 wt. % or 0.05 to 0.5 wt. %,
wt. % with respect to the weight of the whole composition and wherein the components are as described in the present text.

According to another embodiment, the dental adhesive composition of the present text comprises:
ethylenically unsaturated component(s) with acidic moiety: 3 to 20 wt. %,
ethylenically unsaturated component(s) without acidic moiety: 30 to 60 wt. %,
water: 5 to 15 wt. %,
sensitizer(s): 0.6 to 2 wt. %,
reducing agent(s): 0.6 to 2 wt. %,
non-surface treated filler: 5 to 20 wt. %,
(meth)acrylate functional silane: 1 to 4 wt. %,
amino functional silane: 1 to 2 wt. %,
solvent(s): 1 to 20 wt. %,
additive(s): 0.05 to 0.5 wt. %,
wt. % with respect to the weight of the whole composition and wherein the components are as described in the present text.

Such compositions are in particular useful as universal dental adhesive, i.e. an adhesive which can be used as or for direct placement indications, bonding light-cured composite or compomer materials, root surface desensitization, sealing of dentin prior to amalgam restorations, bonding sealants, bonding resin cements, bonding veneers, adhesive primer, and/or sealing of dentin prior to temporization for indirect restoration placement.

According to another embodiment, the dental adhesive composition of the present text comprises:
ethylenically unsaturated component(s) with a phosphoric acidic moiety in an amount of 1 to 5 wt. % or 2 to 3 wt. %,
ethylenically unsaturated component(s) without acidic moiety in an amount of 0 to 5 wt. % or 1 to 3 wt. %,
water in an amount of 0.5 to 5 wt. % or 1 to 3 wt. %,
sensitizer(s) containing an alpha di-keto, anthraquinone, thioxanthone or benzoin moiety in an amount of 0 to 0.5 wt. % or 0.1 to 0.3 wt. %,
reducing agent(s) selected from tert. amines in an amount of 0 to 0.5 wt. % or 0.1 to 0.3 wt. %,
non-surface treated filler selected from silica, zirconia, silca-zirconia and mixtures thereof in an amount of 0 to 2 wt. % or 0.1 to 0.7 wt. %,
(meth)acrylate functional silane selected from (meth)acryloxypropyl trimethoxysilane, (meth)acryloxypropyl triethoxysilane, (meth)acryloxyoctyl trimethoxysilane, (meth)acryloxyoctyl triethoxysilane, (meth)acryloxymethyl trimethoxysilane in an amount of 0.5 to 3 wt. % or 1 to 2 wt. %,
amino functional silane selected from aminopropyl trimethoxysilane, aminopropyl triethoxysilane, N-aminoethyl aminopropyl trimethoxysilane, N-aminoethyl aminopropyl triethoxysilane in an amount of 0.5 to 3 wt. % or 1 to 2 wt. %,
solvent(s) selected from ethanol, n-propanol, isopropanol, acetone, ethyl acetate and mixtures thereof in an amount of 70 to 95 wt. % or 80 to 90 wt. %,
additive(s) in an amount of 0 to 1 wt. % or 0.1 to 0.5 wt. %,
wt. % with respect to the weight of the whole composition.

According to another embodiment, the dental adhesive composition of the present text comprises:
ethylenically unsaturated component(s) with a phosphoric acidic moiety in an amount of 2 to 5 wt. %,
ethylenically unsaturated component(s) without acidic moiety in an amount of 1 to 5 wt. %,
water in an amount of 1 to 5 wt. %,
sensitizer(s) containing an alpha di-keto, anthraquinone, thioxanthone or benzoin moiety in an amount of 0.1 to 0.5 wt. %,
reducing agent(s) selected from tert. amines in an amount of 0.1 to 0.5 wt. %,
non-surface treated filler selected from silica, zirconia, silca-zirconia and mixtures thereof in an amount of 0.1 to 2 wt. %,
(meth)acrylate functional silane selected from (meth)acryloxypropyl trimethoxysilane, (meth)acryloxypropyl triethoxysilane, (meth)acryloxyoctyl trimethoxysilane, (meth)acryloxyoctyl triethoxysilane, (meth)acryloxymethyl trimethoxysilane in an amount of 0.5 to 3 wt. %,
amino functional silane selected from aminopropyl trimethoxysilane, aminopropyl triethoxysilane, N-aminoethyl aminopropyl trimethoxysilane, N-aminoethyl aminopropyl triethoxysilane in an amount of 0.5 to 3 wt. %, solvent(s) selected from ethanol, n-propanol, isopropanol, acetone, ethyl acetate and mixtures thereof in an amount of 70 to 95 wt. %, additive(s) in an amount of 0 to 1 wt. %, wt. % with respect to the weight of the whole composition.

Such compositions are in particular useful as ceramic primer, i.e. for priming surfaces of ceramic articles, such as ceramic articles comprising zirconia, alumina, feldspathic glass ceramic, lithium or disilicate ceramic.

The dental adhesive composition described in the present text can be produced as follows:

providing the components of the dental adhesive composition, mixing the components.

The temperature at which the process can be conducted is not particularly limited.

The temperature used should be below the boiling point of the composition at normal pressure (1013 mbar). Usually the process can be conducted at a temperature in the range of 5° C. to 100° C. or within a range of 10° C. to 80° C. Conducting the process under ambient temperature (e.g. about 23° C.) has been found possible as well.

The atmosphere under which the process of the invention can be conducted is not particularly limited, either.

Usually, the processes are conducted under ambient conditions. Depending on the components used, conducting the process under inert conditions can be recommended. In this respect a nitrogen or argon atmosphere could be useful.

The pressure under which the process of the invention can be conducted is not particularly limited, either. However, the process is typically conducted under ambient pressure (about 1013 mbar).

The reaction mixture should be stirred until a homogeneous dispersion or solution is obtained. Depending on the reaction conditions, this can be accomplished within a few hours (e.g. at least about 1 or at least about 5 or at least about 10 h) or a few days (e.g. at least about 1 or at least about 2 days). A time range within 2 to 20 h can be useful. The pH-value of the reaction mixture depends on the components chosen.

E.g., the pH-value of the reaction mixture can be influenced by the amount of the ethylenically unsaturated component(s) with acidic moiety, the amino functional silane, or the reducing agent (preferably an amine compound) added.

The process is preferably carried out under acidic (pH<7) conditions. Basic conditions could lead to uncontrolled condensation and precipitation of silanes. The manner how the components are added is not particularly limited.

However, if possible, the individual components should be added to the composition in a manner that precipitation of components (e.g., formation of insoluble salts of basic and acidic components) is avoided.

The composition is preferably mixed during its preparation. Mixing or dispersing of components can be accomplished using a device such as magnetic stirrer, mechanical stirrer, dissolver, ball mill, attritor mill or high shear equipment.

A process where a non surface-treated filler is combined with a functional silane, an ethylenically unsaturated acidic component and initiator in the presence of water is sometimes referred to as in-situ silanization. Such a process is described in U.S. Pat. No. 8,710,115 B2 (Thalacker et a.).

For storage, the dental adhesive composition described in the present text is typically packaged in a suitable packaging device.

The dental adhesive composition is typically provided as a one-part composition. That is, all components of the composition are present together during storage and use. No mixing of different parts of the composition is required for application.

Suitable packaging devices include vials, bottles, blisters, syringes, foil pouches, and cartridges.

If desired, the dental adhesive composition can also be provided in a single-use package.

Suitable vials are described e.g. in U.S. Pat. No. 5,996,796 (Kvitrud et al.) and WO 2011/056814 A1 (3M).

The dental adhesive composition may also be stored in a container formed by two sheets, interconnected by hot sealing and cooperating to form a compartment for receiving the liquid and a pocket for receiving a brush i.e. a blister. These kinds of devices are described e.g. in U.S. Pat. No. 6,105,761.

The volume of the packaging device is typically in the range of 0.1 to 100 ml or 0.5 to 50 ml or 1 to 30 ml.

If the packaging device is intended for a single use only, the volume is typically in the range of 0.03 to 2 ml or 0.06 to 1 ml or 0.08 to 0.3 ml.

Described is also a kit of parts comprising the dental adhesive composition described in the present text and one or more of the following items:

dental filling material,
dental milling block,
dental cement,
instruction of use.

A dental filling material is a material which is used for restorative purposes, i.e. for filling cavities in dental tooth structure. A variety of dental filling materials is commercially available including Filtek™ Bulk Fill, Filtek™ Supreme XTE, Filtek™ Z250 (3M Oral Care).

A dental milling block is a block from which dental restorations like dental crowns and bridges can be machined. Dental milling blocks are commercially available, e.g. from 3M Oral Care (Lava™ Plus).

Dental cements are used for fixing dental restorations to dental surfaces, as luting agents, cavity-lining materials and other purposes. Dental cements are typically provided as powder/liquid system or paste/paste system. A variety of dental cements is commercially available, such as RelyX™ Unicem or RelyX™ Ultimate (3M Oral Care).

The instruction of use typically contains a description of the process steps the practitioner should follow when using the dental adhesive composition described in the present text.

The dental composition described in the present text is in particular useful for adhesively fixing a dental restoration to a dental surface. The dental adhesive composition described in the present text is typically used as follows:

The dental adhesive composition is applied either to the surface of a dental restorative material or a dental surface.

The dental restorative material typically has the shape of a dental crown, dental bridge, dental post, dental veneer, dental inlay, dental onlay, dental implant, dental filling, fixed or removable denture, orthodontic appliance (e.g. a bracket, ring or retainer) or part thereof.

The material of the dental restoration includes metal (e.g. gold, dental alloys), zirconia, feldspathic glass ceramic, lithium disilicate ceramic, composite, alumina, porcelain fused to metal, or composite veneered metal.

Dental restorations based on zirconia are described in WO 2012/125885 A1 (3M). Commercially available products are e.g. Lava™ Plus (3M Oral Care).

Dental restorations based on feldspathic glass ceramic are described in U.S. Pat. No. 4,798,536 (Katz). Commercially available products are e.g. VitaBlocs™ Mark II (VITA Zahnfabrik).

Dental restorations based on lithium disilicate ceramic are described in US 2015/374465 (Burke et al.). Commercially available products are e.g. Emax™.CAD (Ivoclar-Vivadent).

The dental adhesive composition described in the present text can also be used as self-etching adhesive composition.

According to one possible use, the dental adhesive composition is applied to the tooth surface, typically in an amount sufficient to etch and prime dental tissue.

In this respect, the following steps are generally applied:
a) applying the dental adhesive composition described in the present text to the surface of a tooth (enamel and/or dentin), preferably using a brush or a sponge, the surface of the tooth can be prepared, etched with an acid (e.g. phosphoric acid) or as it is,
b) optionally dispersing the dental adhesive composition to a thin film, preferably using a stream of air,
c) light initiated curing of the dental adhesive composition, the light having a wave length in range of e.g. 300 nm to 800 nm, and
d) optionally applying a dental filling composition, a dental luting cement or an orthodontic adhesive.

According to another possible use, the dental adhesive composition is applied to the surface of a dental restoration.

The surface of the dental restoration may have been surface treated before. Suitable surface treatments include etching (e.g. with strong acids like hydrofluoric acid) or sandblasting.

In this respect the following steps are generally applied:
a) providing a dental restoration,
b) pre-treating a part of the surface of the dental restoration,
c) applying the dental adhesive composition described in the present text to the pre-treated surface of the dental restoration, preferably by using a brush or a sponge,
d) optionally dispersing the dental adhesive composition to a thin film, preferably using a stream of air,
e) optionally light initiated curing of the dental adhesive composition, the light having a wave length in range of e.g. 300 nm to 800 nm, and
f) optionally applying a dental filling composite or a dental luting cement on the dental adhesive composition.
g) optionally shaping the filling composite and light curing it (e.g. in the case of repairing a dental restoration), or
h) optionally seating the dental restoration together with the luting cement on the site of a preparation (e.g. in the case of cementation of a restoration), and
i) optionally light curing the luting cement and the dental adhesive composition through the restoration material.

The silane composition described in the present text, i.e. the combination of (meth)acrylate functional silane(s) and an amino function silane(s), is in particular useful for improving the adhesion of a dental adhesive composition as described in the present text to feldspathic glass ceramic or lithium disilicate ceramic materials.

All components used in the dental composition of the invention should be sufficiently biocompatible, that is, the composition should not produce a toxic, injurious, or immunological response in living tissue.

The dental adhesive composition does typically not comprise halogenated solvents and/or solvents with a boiling point larger than about 150° C., aldehydes, intensely coloured dyes or pigments which are not photobleachable, fillers with an average particle size larger than about 50 µm, non-agglomerated fillers with a particle size of less about than 20 nm.

According to one embodiment the dental adhesive composition described in the present text does not comprise non acidic sulphur containing polymerizable components in an amount above 1 wt. %, with respect to the weight of the whole composition.

According to one embodiment the dental adhesive composition described in the present text does not comprise polyhydrogen fluoride salts in an amount of more than 0.5 or 0.2 or 0.1 or 0.05 wt. %, wt. % with respect to the weight of the whole composition.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. The above specification, examples and data provide a description of the manufacture and use of the compositions and methods of the invention. The invention is not limited to the embodiments disclosed herein. One skilled in the art will appreciate that many alternative embodiments of the invention can be made without departing from the spirit and scope of thereof.

The following examples are given to illustrate, but not limit, the scope of this invention. Unless otherwise indicated, all parts and percentages are by weight.

EXAMPLES

Unless otherwise indicated, all parts and percentages are on a weight basis, all water is de-ionized water, and all molecular weights are weight average molecular weight. Moreover, unless otherwise indicated all experiments were conducted at ambient conditions (23° C.; 50% relative humidity, approximately 1013 mbar).

Methods

Shear Bond Strength (SBS) Testing Method (According to DIN EN ISO 29022:2013-09)

The surface of VitaBlocs™ Mark II (feldspathic glass ceramic, VITA Zahnfabrik) or fired Emax™.CAD (lithium disilicate, Ivoclar-Vivadent) blocks was polished with sandpaper (320 grit) and then etched with hydrofluoric acid (IPS Ceramic Etching Gel, Ivoclar-Vivadent) according to manufacturers' instructions. Adhesive formulations were applied using a microbrush for 20 sec with gentle rubbing. Solvents were removed from the adhesive using a gentle stream of pressurized air (30 kPa) for 5 sec. The adhesive was light cured for 10 sec using an Elipar™ S10 LED light (3M Oral Care). Then a composite button (Filtek™ Z250, 3M Oral Care) was placed on the cured adhesive using a mold and clamp according to DIN EN ISO 29022 (Ultradent) and cured for 20 sec using an Elipar™ S10 LED light (3M Oral Care). Specimens were stored in water at 36° C. for 24 hours or subject to artificial aging (5,000 thermal cycles, 5° C.-55° C., 30 sec dwell time). Shear bond strength (n=10) was measured using a testing machine7 and a jig according to DIN EN ISO 29022.

pH Measurement pH was measured using a Vario pH SET device (WTW, Weilheim, Germany) which was calibrated using the solutions and procedure provided by the manufacturer. The pH was recorded when the display readout remained constant (typically after 5-10 s).

Viscosity

If desired, the viscosity can be measured using a Physica MCR 301 Rheometer (Anton Paar, Graz, Austria) with a cone/plate geometry CP25-1 under controlled shear rate at 23° C. The diameter is 25 mm, the cone angle 1°, and the separation between the cone tip and the plate 49 µm. The shear rate is ramped down logarithmically from $1000\ s^{-1}$ to $1\ s^{-1}$, with a total of 23 data points being collected. The integration time for each data point is 10 s.

Particle Size Distribution

If desired, the particle size can be measured using a Malvern Mastersizer 2000 (Malvern Instruments, Malvern, Worcestershire, UK) light scattering instrument. The Mastersizer 2000 uses an integrated optical system to cover the range from 0.02 to 2000 µm. The mixtures to be analysed is added to the test chamber filled with isopropanol until an obscuration of approximately 8-15% is reached. No ultrasound is applied in order not to alter the particle size distributions. The raw data is processed with the instrument software using a refractive index of 1.459 and applying the Mie correction together with the Fraunhofer approximation, frequently used techniques known to the expert.

Materials

TABLE 1

| Name | Description |
|---|---|
| CPQ | Camphorquinone |
| HEMA | 2-Hydroxyethyl methacrylate |
| MPTS | 3-Methacryloxypropyl trimethoxysilane |
| EDMAB | Ethyl 4-dimethylaminobenzoate |
| BisGMA | Bisphenol A diglycidyl ether dimethacrylate |
| MHP | 6-Methacryloxyhexyl phosphate (cf. e.g., compound "MHP-B" in WO 2005/018581 A2; page 40) |
| A200 | fumed silica with a BET surface area of about 200 $m^2/g$, e.g. Aerosil ™ 200, available from Evonik AG |
| APTS | 3-Aminopropyl trimethoxysilane |
| DMAEMA | N,N'-dimethylaminoethyl methacrylate |

General Process for Producing the Dental Adhesive Composition

The compositions described in Table 2 were produced by mixing the respective components and the shear bond strength was tested as described above.

TABLE 2

| Component [wt %] | CE1 (*) | CE2 | EX1 | EX2 | EX3 | EX4 | EX5 |
|---|---|---|---|---|---|---|---|
| Ethanol | 12.48 | 12.48 | 12.27 | 12.17 | 12.80 | 12.69 | 86.2 |
| Water | 12.48 | 12.48 | 12.27 | 12.17 | 12.80 | 12.69 | 1.0 |
| HEMA | 25.51 | 25.51 | 25.09 | 24.88 | 26.16 | 25.94 | 3.0 |
| BisGMA | 25.51 | 25.51 | 25.09 | 24.88 | 26.16 | 25.94 | 3.0 |
| MPTS | 1.66 | — | 1.64 | 1.62 | 1.71 | 1.69 | 1.7 |
| MHP | 15.60 | 15.60 | 15.34 | 15.21 | 16.00 | 15.86 | 4.0 |
| CPQ | 1.56 | 1.56 | 1.53 | 1.52 | 1.60 | 1.59 | 0.2 |
| EDMAB | 1.04 | 1.04 | 1.02 | 1.01 | 1.07 | 1.06 | 0.2 |
| A200 | 4.16 | 4.16 | 4.09 | 4.06 | — | — | — |
| APTS | — | 1.66 | 1.64 | 1.62 | 1.71 | 1.69 | 0.7 |
| DMAEMA | — | — | — | 0.84 | — | 0.87 | — |
| Sum | 100 | 100 | 100 | 100 | 100 | 100 | 100 |
| pH | 1.6 | 2.1 | 2.0 | 2.7 | 2.0 | 2.7 | 2.4 |
| SBS to lithium disilicate [MPa] (SD) | 22.9 (8.1) | 9.7 (1.5) | 28.6 (4.7) | 39.9 (3.0) | 35.2 (6.8) | 26.8 (5.3) | 33.6 (6.8) |
| SBS to feldspathic glass ceramic [MPa] (SD) | 16.3 (4.0) | 17.4 (1.9) | 19.6 (3-2) | 26.7 (4.0) | 28.7 (5-2) | 22.9 (5.4) | 22.0 (2.2) |

(*) Ex. 1 of U.S. Pat. No. 8,710,115 B2;

CE: Comparative Example;

EX: Inventive Example

As shown, by adding an amino functional silane to the composition of Example 1 of U.S. Pat. No. 8,710,115 B2 (Comparative Example 1) the adhesive strength of the composition to a glass ceramic surface is increased. Further, adding a filler component did not negatively affect the adhesive strength.

If only the amino-functional silane was used, the shear bond strength to lithium disilicate was significantly reduced.

What is claimed is:

1. A dental adhesive composition comprising:
    ethylenically unsaturated component(s) with acidic moiety;
    ethylenically unsaturated component(s) without acidic moiety;
    water;
    sensitizing agent(s);
    reducing agent(s); and
    a silane composition comprising:
        (meth)acrylate functional silane(s), and
        amino functional silane(s),
    wherein the (meth)acrylate functional silane(s) is present in equal proportion or in excess with respect to weight over the amino functional silane(s), and
    wherein the dental adhesive composition exhibits a shear bond strength to hydrofluoric acid etched lithium disilicate and feldspathic dental ceramics of at least 20 MPa according to DIN EN ISO 29022 (2013-09).

2. The dental adhesive composition of claim 1, the (meth)acrylate functional silane being characterized by one or more of the following features:
    Molecular weight: 200 to 400 g/mol;
    Formula:

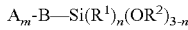

$A_m\text{-}B\text{—}Si(R^1)_n(OR^2)_{3-n}$ wherein:
    A is a (meth)acrylate,
    B is selected from (i) linear or branched $C_1$ to $C_{12}$ alkyl, (ii) $C_6$ to $C_{12}$ aryl, (iii) organic group having 2 to 20 carbon atoms, wherein the organic group comprises one or more ether, thioether, ester, thioester, thiocarbonyl, amide, urethane, carbonyl, and sulfonyl linkages,
    $R^1$ is a $C_1$ to $C_6$ alkyl group, or an $C_6$ to $C_{12}$ aryl group,
    $R^2$ is a $C_1$ to $C_6$ alkyl group,
    m=1, 2, 3, or 4, and
    n=0, 1, or 2.

3. The dental adhesive composition of claim 1, the amino functional silane being characterized by one or more of the following features:
    Molecular weight: 160 to 500 g/mol;
    Formula:

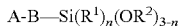

$A\text{-}B\text{—}Si(R^1)_n(OR^2)_{3-n}$ wherein:
    A is an amino moiety,
    B is selected from (i) linear or branched $C_1$ to $C_{12}$ alkyl, (ii) $C_6$ to $C_{12}$ aryl, (iii) organic group having 2 to 20 carbon atoms, wherein the organic group comprises one or more ether, thioether, ester, thioester, thiocarbonyl, amino, amide, urethane, carbonyl, and sulfonyl linkages,
    $R^1$ is a $C_1$ to $C_6$ alkyl group or a $C_6$ to $C_{12}$ aryl group,
    $R^2$ is a $C_1$ to $C_6$ alkyl group, and
    n=0, 1, or 2.

4. The dental adhesive composition of claim 1, wherein:
    ethylenically unsaturated component(s) with acidic moiety is present in an amount of 2 to 20 wt. %,
    ethylenically unsaturated component(s) without acidic moiety is present in an amount of 20 to 60 wt. %,
    water is present in an amount of 5 to 20 wt. %,
    sensitizer(s) is present in an amount of 0.1 to 3 wt. %,
    reducing agent(s) is present in an amount of 0.1 to 3 wt. %,
    (meth)acrylate functional silane is present in an amount of 0.5 to 5 wt. %,
    amino functional silane is present in an amount of 0.2 to 4 wt. %,
    optionally solvent(s) is present in an amount of 0 to 50 wt. %, and
    optionally stabilizers is present in an amount of 0 to 1 wt. %,
    wt. % with respect to the weight of the composition.

5. The dental adhesive composition of claim 1, wherein:
    ethylenically unsaturated component(s) with a phosphoric acidic moiety is present in an amount of 1 to 5 wt. %,
    ethylenically unsaturated component(s) without acidic moiety is present in an amount of 1 to 5 wt. %,
    water is present in an amount of 1 to 5 wt. %,
    sensitizer(s) is present in an amount of 0.1 to 0.5 wt. %,
    reducing agent(s) is present in an amount of 0.1 to 0.5 wt. %,
    non-surface treated filler is present in an amount of 0.1 to 2 wt. %,
    (meth)acrylate functional silane is present in an amount of 0.5 to 3 wt. %,
    amino functional silane is present in an amount of 0.5 to 3 wt. %, and
    solvent(s) is present in an amount of 70 to 95 wt. %,
    wt. % with respect to the weight of the composition.

6. The dental adhesive composition of claim 1, further comprising filler(s) in an amount of 0.1 to 40 wt. %.

7. The dental adhesive of claim 1, being characterized by one or more of the following features:
    Viscosity: 0.01 to 3 Pa*s at 23° C.; and
    pH value: 1 to 5.

8. The dental adhesive composition of claim 1, for use in affixing a dental restoration to a dental surface.

9. A process for treating a dental surface, the process comprising:
    providing a dental adhesive composition of claim 1,
    applying the dental adhesive composition to one or more of the dental surface and a dental restoration.

10. The process of claim 9, the dental restoration having the shape of a dental crown, dental bridge, dental post, dental veneer, dental inlay, dental onlay, dental implant, or any part thereof.

11. The process of claim 9, wherein the dental restoration comprises one or more of the following materials: metal, zirconia, alumina, feldspathic glass ceramic, lithium disilicate ceramic, porcelain fused to metal, and composite veneered metal.

12. A kit comprising:
    a dental adhesive composition of claim 1; and
    one or more of the following parts:
        dental filling material,
        dental milling blank,
        dental cement,
        hydrofluoric acid etchant,
        sandblasting medium, and
        sandblasting device.

13. A process for preparing a dental adhesive composition, the process comprising the steps:
   providing components of a dental adhesive composition of claim 1; and
   mixing the components.

14. The kit of claim 12, wherein the dental adhesive composition is provided as a one-part composition.

* * * * *